United States Patent [19]

Ryder

[11] 4,243,632
[45] Jan. 6, 1981

[54] CONTACT LENS DISINFECTOR WITH TEMPERATURE INDICATOR

[75] Inventor: Francis E. Ryder, Arab, Ala.

[73] Assignee: Ryder International Corporation, Arab, Ala.

[21] Appl. No.: 51,121

[22] Filed: Jun. 22, 1979

[51] Int. Cl.³ .................... C01D 1/32; C01F 1/00; C01B 25/10
[52] U.S. Cl. .................... 422/119; 422/199; 422/300; 116/221; 73/363.5; 40/454
[58] Field of Search ............ 422/292, 119, 199, 300; 116/221; 73/363.5, 363.7; 206/305, 306; 246/169 R, 169 A; 219/438, 419, 441, 510, 512, 521; 40/453, 454

[56] References Cited

U.S. PATENT DOCUMENTS

| | | | |
|---|---|---|---|
| 1,475,430 | 11/1923 | Curwen | 40/454 |
| 1,581,812 | 4/1926 | Ryan et al. | 116/221 |
| 1,816,112 | 7/1931 | Deisch | 116/221 |
| 3,494,321 | 2/1970 | Moore et al. | 116/221 |
| 3,660,919 | 5/1972 | Nagel | 40/454 |
| 3,983,362 | 9/1976 | Hoogenteger et al. | 422/300 |
| 4,141,247 | 2/1979 | Schlick | 116/221 |

Primary Examiner—S. Leon Bashore
Assistant Examiner—Chris Konkol
Attorney, Agent, or Firm—Trexler, Wolters, Bushnell & Fosse, Ltd.

[57] ABSTRACT

A unit (10) for disinfecting contact lenses includes a housing, heating means (20) arranged to heat a contact lens case (21) and the contact lenses therein and means (30) for indicating the temperature condition (HOT or COLD) of the lens case. The temperature indicating means includes a viewing window (17) formed in the housing, a prismatic lens (38) within the housing and behind the viewing window, and pivotally mounted indicia (39) behind the prismatic lens that indicates if the lens case is cool enough to handle following the disinfecting heating cycle.

10 Claims, 5 Drawing Figures

CONTACT LENS DISINFECTOR WITH TEMPERATURE INDICATOR

BACKGROUND OF THE INVENTION

The present invention relates to a contact lens disinfector unit having an improved temperature indicator.

Disinfector units frequently include a lens case which makes broad surface contact with a block that is heated by an electric current. After heating the lenses at a disinfecting temperature for a sufficient time, the application of current to the heating block is terminated and the lens case and contact lenses are allowed to cool and then removed for use.

Disinfector units of the foregoing type have generally controlled the application of electric current to the heating block with a thermocoupled switch. The thermocouple, after detecting a predetermined temperature of the heating block, breaks the switch contact for terminating the application of the electric current. Wired in series with the switch may be a light bulb. The light bulb lights up when the switch is closed and the electric current is being applied to the heating block and is turned off when the thermocouple opens the switch to terminate the application of the electric current to the heating block. Because of this arrangement, the user may not know when the contact lens case has cooled sufficiently to be safely removed. The user may therefore either attempt to remove the lens case too soon resulting in possible injury, or wait an exceedingly long time after the light bulb turns off to be assured that the lens case may be safely removed. As a result, such disinfectors are inconvenient to use and may result in injury to the user.

It is therefore an object of the present invention to provide a new and improved contact lens disinfector unit which includes a temperature indicator for indicating if the contact lens case is hot and unsafe for removal or if the lens case has cooled sufficiently for safe removal.

The present invention therefore provides a contact lens disinfector unit for sterilizing contact lenses contained within a contact lens case. The contact lens disinfector unit includes a housing, heating means arranged to heat the contact lens case and the contact lenses therein to a disinfecting temperature and for terminating the application of heat thereafter to allow the contact lenses to cool, and temperature indicating means for indicating first and second temperatures of the heating means. The temperature indicator may include a viewing window formed in the housing, prismatic lens means within the housing and behind the viewing window, first and second temperature indicia behind the prismatic lens means, wherein the prismatic lens means is arranged for movement such that the first temperature indicia is viewable through the viewing window when the prismatic lens means is at a first angular position relative to the viewing window, and the second temperature indicia is viewable through the viewing window when the prismatic lens means is at a second angular position relative to the viewing window; and actuating means responsive to the temperature of the heating means for moving the prismatic lens means between the first and second angular positions relative to the viewing window.

DESCRIPTION OF THE PREFERRED EMBODIMENT

Figure 1:
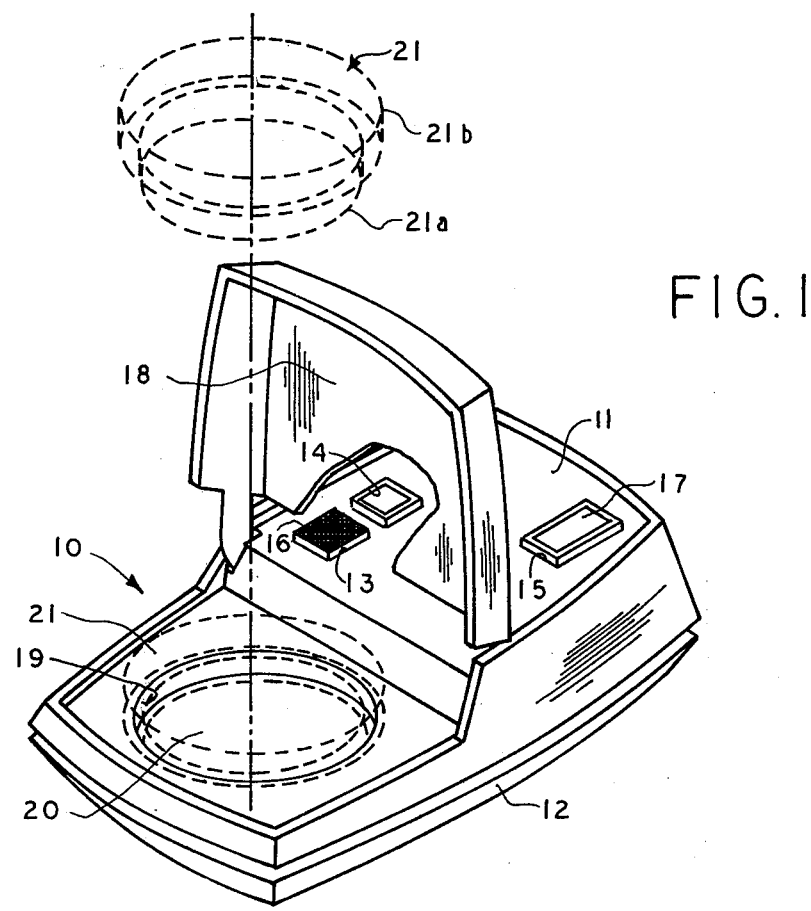
FIG. 1 is a perspective view of a contact lens disinfector unit embodying the present invention showing its hinged cover partially broken away and in a raised position and a contact lens case (in dashed lines) shown both in an exploded position relative to the disinfector unit and in an operative position with respect to the heating arrangement contained within the unit.
Figure 2:
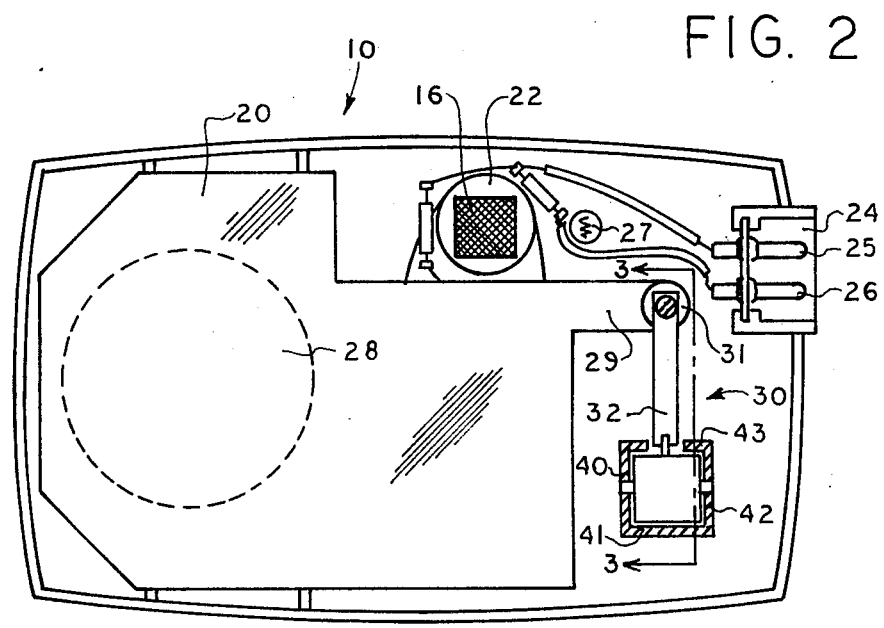
FIG. 2 is a top plan view of the interior of the disinfector unit of FIG. 1, partially in section, the top or cover portion of the unit housing having been removed.

Referring now to FIGS. 1 and 2, the disinfector unit 10 thereshown includes a housing comprised of a top cover section 11, a bottom section 12, the latter being adapted to house removably a lens case 21. The top cover section has openings 13, 14 and 15. In the first opening 13 there is an activator button 16 mechanically coupled to a thermocouple switch 22 such that depressing the button 16 initiates a disinfecting cycle. The second opening 14 is disposed over a light bulb 27 (FIG. 2) which lights when the thermocouple switch 22 is closed, thus indicating that the unit 10 is in the heating mode. The light bulb 27 is extinguished when the thermocouple switch 22 opens upon reaching the proper disinfecting temperature. The opening 15 forms a viewing window 17 through which the user may view a temperature indicating indicia so as to be informed whether or not the contact lens case is sufficiently cool to enable safe removal of the lens case 21 from the disinfector unit.

The top cover section 11 includes a hinged lid portion 18 which is shown in a raised position in FIG. 1, allowing the lens case 21 to be inserted or withdrawn from the housing. In addition, the top cover section 11 includes a circular recess 19 which communicates with the upper surface of a heating block 20 in the unit 10. The recess 19 is conventionally dimensioned for receiving the lens case 21. The lens case 21 may conventionally include a bottom portion 21a removably engaged with an upper portion 21b and is internally designed in a known manner to accommodate a pair of lenses and a quantity of disinfecting solution. Preferably, the lens case 21 and the recess 19 are dimensioned such that the bottom surface of the lens case makes surface-to-surface contact with the upper surface of the heating block 20. During the disinfecting cycle, the heating block 20 provides sufficient heat transfer to the lens case 21 so as to heat the contact lenses and the disinfecting solution to a temperature sufficient to kill pathogenic bacteria on the lenses.

The disinfector unit 10 further includes a power supply circuit for a resistive heating element (not shown) that heats the heating block 20 in a known manner. The power supply circuit is adapted to be connected to an electric power source by the pins 25 and 26 of a connector 24. Thus, in a known manner the disinfecting cycle is initiated by depressing the button 16 to close the thermocouple switch 22 so as to supply current to the heating element that heats the heating block 20. Light 27 is now illuminated and remains so until the desired disinfecting temperature has been reached following which the switch 22 opens and light 27 goes out. At this time, however, the lens case 21 is still too hot to remove from the unit 10.

The heating block 20 includes a surface portion 28 shown in dashed lines (FIG. 2) which engages the under surface of the lens case 21 during the sterilization of the contact lenses. The heating block includes a rearward portion 29 which terminates in upstanding post 31 to which the indicating arrangement 30 is operatively connected. The heating block 20 is in contact with the resistive heating element mentioned above, and due to the surface-to-surface contact with the case 21 applies heat evenly thereto for a sufficient period of time during the disinfecting cycle so as to raise the temperature of the disinfecting solution to that required for disinfecting of the contact lenses.

Figure 3:
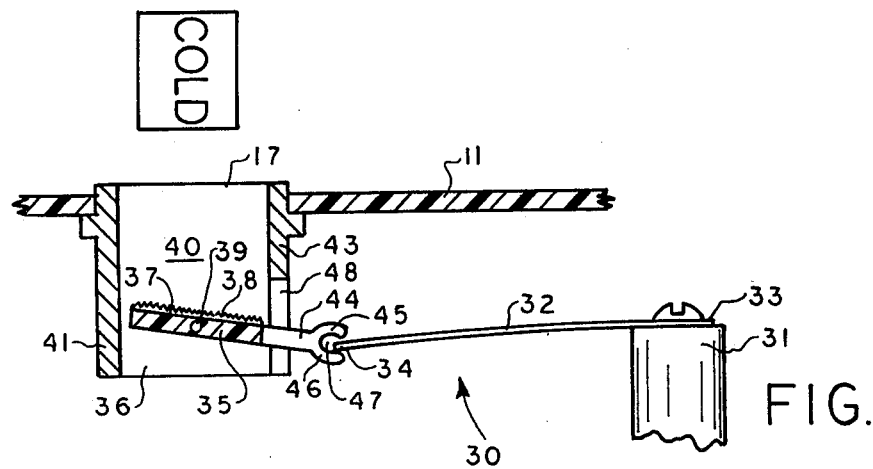
FIG. 3 is a partial cross-sectional view taken generally along lines 3—3 of FIG. 2 illustrating the temperature indicating arrangement of the present invention in a first operative condition.
Figure 4:
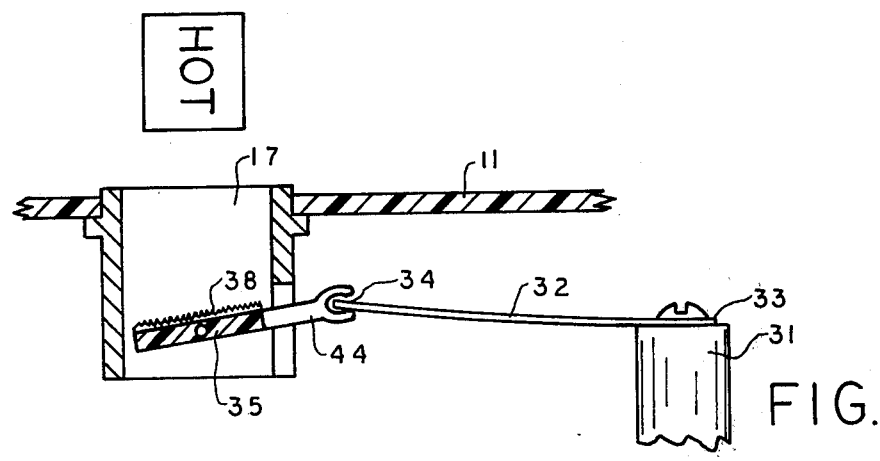
FIG. 4 is a cross-sectional view similar to FIG. 3 but showing the temperature indicating arrangement in a second operative condition.

Attention is now directed to the temperature indicating arrangement 30 which is shown in greater detail in FIGS. 3 and 4. The arrangement includes a temperature sensitive member 32 in the form of a bi-metallic strip which has one end 33 affixed to the upstanding post 31 of the heating block 20 and the other end 34 free to move vertically in first and second directions. The end 34 will move in a first direction upwardly as the temperature of the heating block 20 and lens case 21 rises and downwardly in a second direction as the heating block and lens case cools. As will be described more fully hereinafter, the reciprocal vertical movement of the bi-metallic strip 32 is used to impart pivotal movement to a temperature indicia carrying member 35 which in the illustrated embodiment is in the form of a flat or planar member. The planar member 35 is pivotally mounted within a hollow upstanding column or tunnel member 36 having a plurality of side walls 40, 41, 42 and 43 as best seen in FIG. 2. The planar member 35 is pivotally mounted across opposing side walls 40 and 42 for rocking movement in the member 36. The planar member 35 has a rearward extension 44 (FIGS. 3 and 4) which terminates in a pair of bifurcated opposing members 45 and 46 which define a space 47 therebetween for receiving the free end 34 of the bi-metallic strip 32. The rearward extension 44 extends through an opening 48 in the side wall 43 of tunnel structure 36. The planar member 35 has an upper surface 37 which carries a prismatic lens 38 and temperature indicia 39 therebetween.

Figure 5:
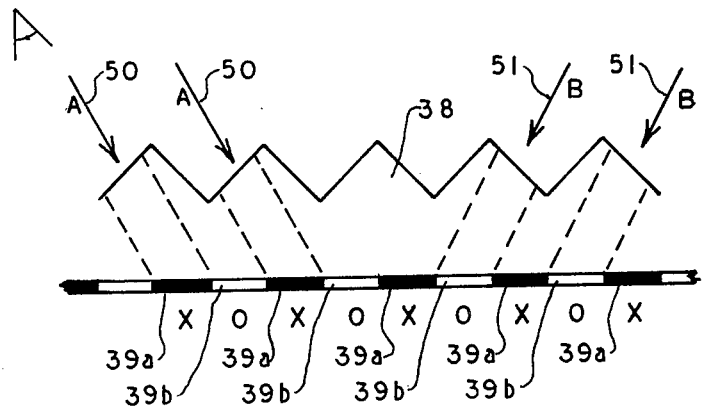
FIG. 5 is a schematic illustration illustrating the operation of the prismatic lens of the temperature indicating arrangement shown in FIGS. 3 and 4.

The prismatic lens and temperature indicia form a so-called "vari-vue" display that changes when tilted or pivoted. In FIG. 5 a prismatic lens 38 and first and second temperature indicia 39a and 39b are shown. The pair of temperature indicia are formed by a plurality of strips wherein the strips 39a of one indicia are alternated with the strips 39b of the other indicia. The strips of each respective indicia, when viewed, form a complete image, which for example, may be a word to indicate the temperature condition of the disinfector unit heating block and lens case. For example, the first temperature indicia strips 39a may combine together to form the word COLD as illustrated in FIG. 3, and the second temperature indicia strips 39b may combine to form the word HOT as seen in FIG. 4.

When the prismatic lens is tilted or pivoted to a first angular position with respect to the viewing window 17, the prismatic lens will be viewed at an angle represented by the arrows 50. As a result, only temperature indicia strips 39a will be viewable through the window so that the user will be informed that the heating block and lens case are sufficiently cooled so that the lens case 21 may be safely removed from the disinfector unit. When the prismatic lens 38 is pivoted to a second angular position relative to the viewing window 17 as illustrated in FIG. 4, the user will view the prismatic lens from an angle illustrated by arrows 51. Hence, only strips 39b of the second temperature indicia will be seen, which will inform the user that the heating block and lens case are too hot to allow the lens case to be safely removed.

At the beginning of a disinfecting cycle, the heating block 20 and contact lens case 21 will be cool and the bi-metallic strip 32 will be disposed in the COLD position as shown in FIG. 3. As the temperature of the heating block and contact lens case rise, the free end 34 of bi-metallic strip 32 will be displaced upwardly so as to cause the planar member 35 and prismatic lens 38 to pivot to the second angular position relative to the viewing window 17 as shown in FIG. 4. When the heating block and lens reach a temperature considered to be excessively hot for safe removal of the lens case 21 from the disinfector unit, the prismatic lens 38 will be disposed in the second or HOT position as shown in FIG. 4.

Upon the cooling of the heating block and lens case following opening of the switch 22, the bi-metallic strip 32 at its free end 34 will once again be displaced downwardly. When the contact lens case reaches a cool safe temperature for removal, the bi-metallic strip will cause the prismatic lens 38 to be disposed at its first angular position once again so that the first temperature indicia word COLD will be viewable through the viewing window 17.

The tunnel 36 is relatively deep and the indicia-carrying member 35 is relatively deeply positioned with the tunnel 36, namely substantially recessed from the viewing window 17. As a result the user must view the member 35 substantially along the central axis of the tunnel 36 or along a path that is only offset at small amounts from the axis of the tunnel 36. Consequently, the field of view through the window 17 is narrow so as to avoid misreading the indicia as might result if the viewing path were too wide.

The invention is claimed as follows:

1. A disinfector unit for disinfecting contact lenses comprising: a housing; heating means arranged to heat the contact lenses to a disinfecting temperature; and temperature indicating means for indicating first and second temperature ranges with respect to a portion of said housing, said temperature indicating means comprising a prismatic lens means, first and second temperature indicia behind said prismatic lens means, and a pivotally mounted member carrying said prismatic lens means and said temperature indicia, said prismatic lens means being arranged for movement such that said first temperature indicia is viewable and the second temperature indicia is obscured when said prismatic lens means is at a first position, and said second temperature indicia is viewable and said first temperature indicia is obscured when said prismatic lens means is at a second position, and temperature responsive means for moving said pivotally mounted member and said prismatic lens means between said first and second positions as a function of the temperature of said housing portion.

2. A disinfector unit as defined in claim 1, wherein said temperature responsive means comprising a bi-metallic strip having a first end secured to said heating means and a second end engaging said pivotal member, said second end being arranged for moving in first and second directions responsive to the temperature of said heating means for pivoting said pivotal member between said first and second positions.

3. A disinfector unit according to claim 1 including a viewing window in said housing, and wherein said first and second positions are angular positions relative to said viewing window.

4. A disinfector unit as defined in claim 3 further including tunnel means having an end wall forming said viewing window and a cavity, and wherein said prismatic lens means is pivotally mounted within said tunnel means.

5. A disinfector unit as defined in claim 4 wherein said tunnel means cavity has a plurality of sidewalls, and wherein said prismatic lens means is pivotally mounted on an opposing pair of said sidewalls.

6. A disinfector unit as defined in claim 5 wherein said pivotally mounted member is mounted across said pair of opposing sidewalls and having a surface generally facing said viewing window, and wherein said mounting member has an extension extending through one of said sidewalls and coupled to said actuating means.

7. A disinfector unit as defined in claim 6 wherein said heating means comprises a heating block, and wherein said actuating means includes a bi-metallic strip having a first end connected to said heating block and a second end coupled to said mounting member extension, said second end being arranged to move in first and second directions responsive to the temperature of said heating block for causing said mounting member and said prismatic lens means and said temperature indicia mounted thereto to pivot between said first and second angular positions relative to said viewing window.

8. For use in a contact lens disinfector of the type having a housing with heating means for heating contact lenses to at least a disinfecting temperature and thereafter for terminating the application of heat allowing the contact lenses to cool, a temperature indicating arrangement comprising: prismatic lens means, first and second temperature indicia disposed behind said lens means, means mounting said lens means for pivotal movement between a first and second angular position for rendering only said first temperature indicia viewable in said housing when said lens means is at said first angular position and for rendering only said second temperature indicia viewable in the housing when at said second angular position, and actuating means responsive to the temperature of said heating means for moving said lens means between said first and second angular positions.

9. A structure as defined in claim 8 wherein said lens means includes a substantially planar under-surface, wherein said first and second temperature indicia are affixed to said lens means under-surface and wherein each said indicia comprises a plurality of segment strips arranged side-by-side and wherein said strips one of said indicia alternate with said strips of said other indicia.

10. A contact lens disinfector unit for sterilizing contact lenses contained within a contact lens case comprising: a housing; a heating block arranged to contact the lens case for heating the contact lenses to a disinfecting temperature and for thereafter terminating the application of heat for allowing the contact lenses to cool; and heating block temperature indicating means for indicating first and second temperatures of said heating block comprising, a vertical hollow column having a plurality of sidewalls including a pair of opposing sidewalls and a top surface defining a viewing window formed in said housing, prismatic lens means having a substantially planar under-surface within said column, first and second temperature indicia affixed to said prismatic lens means under-surface, a pivotal member pivotally mounted between said pair of opposing sidewalls and having an upper surface carrying said prismatic lens means and said temperature indicia and having an extension extending through one of said column sidewalls, said pivot member being pivotal between first and second angular positions for rendering said first temperature indicia visible through said lens means and said window when at said first angular position and for rendering said second temperature indicia visible through said lens means and said window when at said second angular position, and a bi-metallic strip having a first end connected to said heating block and a second end coupled to said pivotal member extension and arranged for reciprocating movement responsive to the temperature of said heating block for pivoting said pivotal member between said first and second angular positions.

* * * * *